(12) United States Patent
Tanaka et al.

(10) Patent No.: US 9,698,320 B2
(45) Date of Patent: Jul. 4, 2017

(54) MODIFIED PRODUCT OF POLYHEDRAL STRUCTURE POLYSILOXANE, POLYHEDRAL STRUCTURE POLYSILOXANE COMPOSITION, CURED PRODUCT, AND OPTICAL SEMICONDUCTOR DEVICE

(75) Inventors: Hiroyuki Tanaka, Osaka (JP); Takao Manabe, Osaka (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 13/823,497

(22) PCT Filed: Sep. 13, 2011

(86) PCT No.: PCT/JP2011/070854
§ 371 (c)(1),
(2), (4) Date: May 22, 2013

(87) PCT Pub. No.: WO2012/039322
PCT Pub. Date: Mar. 29, 2012

(65) Prior Publication Data
US 2013/0237663 A1    Sep. 12, 2013

(30) Foreign Application Priority Data

Sep. 22, 2010 (JP) ................. 2010-211887
Mar. 23, 2011 (JP) ................. 2011-064641

(51) Int. Cl.
| | | |
|---|---|---|
| H01L 33/56 | (2010.01) | |
| C07F 7/21 | (2006.01) | |
| C08G 77/50 | (2006.01) | |
| C08G 77/00 | (2006.01) | |
| C08K 5/3492 | (2006.01) | |
| C08K 5/56 | (2006.01) | |
| C08G 77/04 | (2006.01) | |
| C08G 77/12 | (2006.01) | |
| C08G 77/20 | (2006.01) | |

(52) U.S. Cl.
CPC ............... *H01L 33/56* (2013.01); *C07F 7/21* (2013.01); *C08G 77/50* (2013.01); *C08G 77/80* (2013.01); *C08K 5/34924* (2013.01); *C08K 5/56* (2013.01); *C08G 77/045* (2013.01); *C08G 77/12* (2013.01); *C08G 77/20* (2013.01); *C08K 2201/008* (2013.01)

(58) Field of Classification Search
USPC ............................. 524/588; 526/279; 556/460
See application file for complete search history.

(56) References Cited

U.S. PATENT DOCUMENTS

| | | |
|---|---|---|
| 4,618,657 A | 10/1986 | Katchko et al. |
| 5,047,492 A | 9/1991 | Weidner et al. |
| 5,160,787 A | 11/1992 | Gaku et al. |
| 5,939,576 A | 8/1999 | Lichtenhan et al. |
| 6,127,503 A | 10/2000 | Fujioka et al. |
| 6,252,030 B1 | 6/2001 | Zank et al. |
| 6,623,711 B2 * | 9/2003 | Lyu et al. ........ 423/12 |
| 8,299,198 B2 | 10/2012 | Manabe et al. |
| 8,399,592 B2 | 3/2013 | Manabe et al. |
| 2003/0105246 A1 | 6/2003 | Andoh et al. |
| 2004/0116566 A1 | 6/2004 | Fehn |
| 2005/0173780 A1 | 8/2005 | Sethumadhavan et al. |
| 2006/0052623 A1 | 3/2006 | Yoshida et al. |
| 2006/0074213 A1 | 4/2006 | Kiyomori et al. |
| 2006/0122351 A1 * | 6/2006 | Laine et al. ............ 528/31 |
| 2007/0045619 A1 | 3/2007 | Park et al. |
| 2007/0088094 A1 * | 4/2007 | Tamaki et al. ............. 522/99 |
| 2008/0020213 A1 | 1/2008 | Lichtenhan et al. |
| 2008/0090986 A1 * | 4/2008 | Khanarian ............. C08G 77/52 528/15 |
| 2009/0225640 A1 * | 9/2009 | Manabe et al. ............. 369/100 |
| 2010/0063221 A1 | 3/2010 | Manabe et al. |
| 2010/0099790 A1 * | 4/2010 | Manabe et al. ............. 522/172 |
| 2011/0001190 A1 * | 1/2011 | Ide et al. ................ 257/347 |
| 2011/0251357 A1 * | 10/2011 | Laine et al. .............. 525/478 |
| 2013/0131264 A1 | 5/2013 | Nishiyama et al. |

(Continued)

FOREIGN PATENT DOCUMENTS

| | | |
|---|---|---|
| CN | 101548398 A | 9/2009 |
| CN | 101568546 A | 10/2009 |

(Continued)

OTHER PUBLICATIONS

Li et al. (Polyhedral Oligomeric Silsesquioxanes (POSS) Polymers and Copolymers: A Review, Journal of Inorganic and Organometallic Polymers, 11(3), 123-154, Sep. 2001).*
Machine Translation of JP2004-175887.*
Lin et al (Chapter 18, LED and Optical Device Pagakaging and Materials from Materials for Advanced Packaging, 2009, p. 666).*
Velderrain, M and Lipps, N. (Moisture Permeability of Silicone Systems Guidleines for Choosing a Silicone based on Water Vapor Transmission Rates for Barrier Applications, NuSil Technology, Mar. 4, 2011).*
Zhang, ("The Permeability Characteristics of Silicone Rubber", 2006 SAMPE Fall Technical Conference, "Global Advances in Materials and Process Engineering", proceedings, Coatings and Sealants Section, Nov. 6-9, 2006, Dallas, TX).*

(Continued)

*Primary Examiner* — Christopher M Rodd
(74) *Attorney, Agent, or Firm* — Polsinelli PC

(57) ABSTRACT

An object of the present invention is to provide a polyhedral polysiloxane composition that has high heat resistance and high light resistance, is excellent in gas-barrier properties and thermal shock resistance, and exhibits good handleability when used to encapsulate an optical semiconductor device. The polyhedral polysiloxane composition of the present invention is characterized by including a modified polyhedral polysiloxane which is obtained by hydrosilylation of an alkenyl group-containing polyhedral polysiloxane compound (a) and a hydrosilyl group-containing compound (b) and has a structure derived from an organic silicon compound (a') having one alkenyl group per molecule.

16 Claims, No Drawings

(56) References Cited

U.S. PATENT DOCUMENTS

| | | |
|---|---|---|
| 2013/0165611 A1 | 6/2013 | Manabe et al. |
| 2013/0192491 A1 | 8/2013 | Nishiyama et al. |

FOREIGN PATENT DOCUMENTS

| | | | |
|---|---|---|---|
| EP | 0348705 A2 | | 1/1990 |
| EP | 2151443 A1 | | 2/2010 |
| JP | H0-2-67290 A | | 3/1990 |
| JP | 06-329687 | | 11/1994 |
| JP | 11-071462 A | | 3/1999 |
| JP | 11-124502 | | 5/1999 |
| JP | 2000-154252 A | | 6/2000 |
| JP | 2000-265066 A | | 9/2000 |
| JP | 2002-363414 A | | 12/2002 |
| JP | 2003-137944 A | | 5/2003 |
| JP | 2004-123936 A | | 4/2004 |
| JP | 2004143449 A | | 5/2004 |
| JP | 2004175887 A | * | 6/2004 |
| JP | 2004529984 A | | 9/2004 |
| JP | 2004359933 A | | 12/2004 |
| JP | 200523256 | | 1/2005 |
| JP | 2005-290352 A | | 10/2005 |
| JP | 2006-022207 A | | 1/2006 |
| JP | 2006-104235 A | | 4/2006 |
| JP | 2006-131850 A | | 5/2006 |
| JP | 2006233155 A | | 9/2006 |
| JP | 2006-265514 A | | 10/2006 |
| JP | 2006269402 A | | 10/2006 |
| JP | 2006-299149 A | | 11/2006 |
| JP | 2006-299150 A | | 11/2006 |
| JP | 2007-031619 A | | 2/2007 |
| JP | 2007091935 A | | 4/2007 |
| JP | 2007-169427 A | | 7/2007 |
| JP | 2008-163260 A | | 7/2008 |
| JP | 2008291137 A | | 12/2008 |
| JP | 2009-173759 A | | 8/2009 |
| JP | 2009-173789 A | | 8/2009 |
| JP | 2009-206124 A | | 9/2009 |
| JP | 2010-031254 A | | 2/2010 |
| JP | 2010095616 A | | 4/2010 |
| JP | 2010-254927 A | | 11/2010 |
| JP | 2010-265410 A | | 11/2010 |
| JP | 2011-006546 A | | 1/2011 |
| JP | 2011-016968 A | | 1/2011 |
| JP | 2011-042732 A | | 3/2011 |
| JP | 2011-068753 A | | 4/2011 |
| JP | 2012180513 A | | 9/2012 |
| WO | WO-03042292 A2 | | 5/2003 |
| WO | WO-2004011525 A1 | | 2/2004 |
| WO | WO-2004022231 A1 | | 3/2004 |
| WO | WO-2004024741 A1 | | 3/2004 |
| WO | WO-2006062219 A1 | | 6/2006 |
| WO | WO-2007/022367 A2 | | 2/2007 |
| WO | WO-2008/010545 A1 | | 1/2008 |
| WO | WO-2008/063884 A1 | | 5/2008 |
| WO | WO-2008/066116 A1 | | 6/2008 |
| WO | WO-2008/133138 A1 | | 11/2008 |
| WO | WO-2011-148896 A1 | | 12/2011 |

OTHER PUBLICATIONS

Velderrain, "Moisture Permability of Silicone Systems Case Study #1: Water Vapor Transmission Rate as Influenced by Durmoeter, Silica and Organic-Siloxane Group" NuSil Technology Technical Publication, Jun. 24, 2009.*

Velderrain, "Designing low permeability, optical-grade silicone systems—Guidelines for choosing a silicone based on transmission rates for barrier applications", NuSil Technology Technical Publication, Jan. 26, 2012.*

Riegler et al. "Phosphors and Silicone Dispersions", Nu Sil Technical Report, Mar. 2, 2005.*

Mason, et al. The Settling of Small Particles in a Fluid, Physical Review, 23, 412, Mar. 1, 1924.*

Zhang et al., "Highly Porous Polyhedral Silsesquioxane Polymers. Synthesis and Characterization", J. Am. Chem. Soc. 1998, 120, 8380-8391.

Laine et al., "Polyfunctional Cubic Silsesquioxanes as Building Blocks for Organic/Inorganic Hybrids", Applied Organometal. Chem. 1998, 12, 715-723.

Sellinger et al., "Silsesquioxanes as Synthetic Platforms. Thermally Curable and Photocurable Inorganic/Organic Hybrids", Macromolecules 1996, 29, 2327-2330.

Translation of Notification of Transmittal of Translation of the International Preliminary Report on Patentability (Form PCT/IB338) of International Application No. PCT/JP2007/064233 mailed Feb. 5, 2009 with forms PCT/IB/373 and PCT/ISA/237.

International Preliminary Report on Patentability (Form PCT/IB/373) of International Application No. PCT/JP2011/061757 mailed Dec. 4, 2012 with Form PCT/ISA/273, English translation only.

International Search Report of PCT/JP2007/064233 mailed Oct. 9, 2007.

International Search Report of PCT/JP2011/061757 mailed Sep. 6, 2011.

International Preliminary Report on Patentability (Form PCT/IB/373) or International Application No. PCT/JP2008/057415 mailed Nov. 10, 2009 with Form PCT/ISA/273, English translation only.

International Preliminary Report on Patentability (Form PCT/IB/373) of International Application No. PCT/JP2011/070854 mailed Apr. 16, 2013 with Form PCT/ISA/273, English translation only.

Velderrain et al., "Moisture Permeability of Silicone Systems, Case Study #2, Guidelines for Choosing a Silicon Based on Water Vapor Transmission Rates for Barrier Application", NuSil Silicone Technology, Mar. 4, 2011.

Zhang et al., "The Permeability Characteristics of Silicone Rubber", Society for the Advancement of Material and Process Engineering Fall Technical Conference, Nov. 6-9, 2006.

Jaffres et al., "Synthesis of highly functionalised dendrimers based on polyhedral silsesquioxane cores", J. Chem. Soc., Dalton Trans., 1998, pp. 2767-2770, XP002262722.

* cited by examiner

MODIFIED PRODUCT OF POLYHEDRAL STRUCTURE POLYSILOXANE, POLYHEDRAL STRUCTURE POLYSILOXANE COMPOSITION, CURED PRODUCT, AND OPTICAL SEMICONDUCTOR DEVICE

CROSS REFERENCE TO RELATED APPLICATIONS

This application is a National Phase filing under 35 U.S.C. §371 of PCT/JP2011/070854 filed on Sep. 13, 2011; and this application claims priority to Application No. 2010-211887 filed in Japan on Sep. 22, 2010, and Application No. 2011-064641 filed in Japan on Mar. 23, 2011 under 35 U.S.C. §119; the entire contents of all are hereby incorporated by reference.

TECHNICAL FIELD

The present invention relates to a modified polyhedral polysiloxane, a polyhedral polysiloxane composition, a cured product, and an optical semiconductor device.

BACKGROUND ART

Polysiloxane compositions are used in various industries because of their excellence in heat resistance, cold resistance, weather resistance, light resistance, chemical stability, electrical characteristics, flame retardancy, water resistance, transparency, colorability, anti-adhesive properties, and anti-corrosive properties. In particular, compositions containing polyhedral polysiloxanes are known to have even better properties due to the unique chemical structures of the polyhedral polysiloxanes, such as greater heat resistance, greater light resistance, greater chemical stability, and lower dielectric properties.

Applications of polyhedral polysiloxanes have been proposed, and some of them are intended as encapsulants for optical semiconductor devices. For example, Patent Literature 1 discloses a polyhedral polysiloxane composition containing a polyhedral polysiloxane resin having at least two oxetanyl groups, an aliphatic hydrocarbon having at least one epoxy group, and a cationic polymerization initiator. This material has a high refractive index and high light extraction efficiency. However, the polysiloxane composition of Patent Literature 1 has problems attributed to the oxetanyl and epoxy groups, such as low heat resistance and low light resistance.

In order to deal with these problems, Patent Literature 2, for example, uses an epoxy group-containing polyorganopolysiloxane with the limited glass transition temperature to improve the problems in heat resistance and light resistance. This material is also thought to be more resistant to cracking even after a thermal shock test.

However, it is still difficult to use this material in applications requiring high heat resistance and high light resistance (e.g. white LEDs), and its thermal shock resistance is not high enough.

Additionally, despite the above excellent properties, polysiloxane compositions generally have the problem of low gas-barrier properties. Unfortunately, because of this problem, these compositions, when used as encapsulants for optical semiconductor devices, may allow sulfides to turn reflectors black. An exemplary strategy to deal with this problem is to coat metal members with an acrylic resin having high gas-barrier properties in advance before encapsulating them with a silicone resin as disclosed in Patent Literature 3.

However, the silicone resin used in this technique itself has low gas-barrier properties, and additionally, this technique is problematic in terms of productivity because it requires extra steps such as encapsulation with a silicone resin separately after the coating treatment with an acrylic resin.

In the field of encapsulants for optical semiconductor devices, for example, the following techniques are employed: encapsulants containing a yellow phosphor are used for blue light emitting devices in order to produce white light; or encapsulants containing green and red phosphors are used for blue light emitting devices in order to improve color rendition. When these encapsulants have low viscosity, the phosphors may settle during the handling of the encapsulants to cause the problem of variation in emission color.

For example, Patent Literature 4 discloses a composition containing a modified polyhedral polysiloxane which has excellent moldability/processability, transparency, heat and light resistance, and adhesion. However, this material still leaves room for improvement in terms of the viscosity (handleability) of the composition and gas-barrier properties.

As described above, there is a need to develop materials that have high heat resistance and high light resistance, are excellent in thermal shock resistance and gas-barrier properties, and exhibit good handleability when used to encapsulate an optical semiconductor device.

CITATION LIST

Patent Literature

Patent Literature 1: JP-A 2008-163260
Patent Literature 2: JP-A 2007-169427
Patent Literature 3: JP-A 2009-206124
Patent Literature 4: WO 2008/010545

SUMMARY OF INVENTION

Technical Problem

The present invention provides a polyhedral polysiloxane composition that has high heat resistance and high light resistance, is excellent in gas-barrier properties and thermal shock resistance, and exhibits good handleability when used to encapsulate an optical semiconductor device or the like; a modified polyhedral polysiloxane for such a composition; and a cured product and an optical semiconductor device including such a composition.

Solution to Problem

The present inventors have made intensive studies to solve the above problems, and finally completed a modified polyhedral polysiloxane, a polyhedral polysiloxane composition, a cured product, and an optical semiconductor device which have features described below.

(1) A modified polyhedral polysiloxane, which is obtained by hydrosilylation of an alkenyl group-containing polyhedral polysiloxane compound (a) and a hydrosilyl group-containing compound (b), and has a structure derived from an organic silicon compound (a') having one alkenyl group per molecule.

(2) The modified polyhedral polysiloxane of (1), which is in liquid form at 20° C.

(3) The modified polyhedral polysiloxane of (1) or (2), wherein the organic silicon compound (a') having one alkenyl group per molecule has at least one aryl group.

(4) The modified polyhedral polysiloxane of (3), wherein the aryl group is directly bonded to a silicon atom.

(5) The modified polyhedral polysiloxane of any of (1) to (4), wherein the hydrosilyl group-containing compound (b) is at least one of a hydrosilyl group-containing cyclic siloxane and a hydrosilyl group-containing linear siloxane.

(6) The modified polyhedral polysiloxane of any of (1) to (4), wherein the hydrosilyl group-containing compound (b) is a hydrosilyl group-containing cyclic siloxane.

(7) The modified polyhedral polysiloxane of (6), wherein the hydrosilyl group-containing compound (b) is 1,3,5,7-tetrahydrogen-1,3,5,7-tetramethylcyclotetrasiloxane (8) The modified polyhedral polysiloxane of any of (1) to (7), wherein the alkenyl group-containing polyhedral polysiloxane compound (a) is an alkenyl group-containing polyhedral polysiloxane compound containing a siloxane unit represented by the formula:

$$[AR^1{}_2SiO\text{—}SiO_{3/2}]_a[R^2{}_3SiO\text{—}SiO_{3/2}]_b$$

wherein a+b is an integer of 6 to 24, provided that a is an integer of 1 or larger and b is an integer of 0 or 1 or larger; A is alkenyl; $R^1$ is alkyl or aryl; and $R^2$ is hydrogen, alkyl, aryl or a group bonded to another polyhedral polysiloxane.

(9) A modified polyhedral polysiloxane, containing a siloxane unit represented by the formula:

$$[XR^3{}_2SiO\text{—}SiO_{3/2}]_a[R^4{}_3SiO\text{—}SiO_{3/2}]_b$$

wherein a+b is an integer of 6 to 24, provided that a is an integer of 1 or larger and b is an integer of 0 or 1 or larger; $R^3$ is alkyl or aryl; $R^4$ is alkenyl, hydrogen, alkyl, aryl, or a group bonded to another polyhedral polysiloxane; and X has a structure represented by the following formula (1) or (2), and in the case where multiple Xs are present, the structures of the formula (1) or (2) may be different from one another and the structures of the formulas (1) and (2) may coexist:

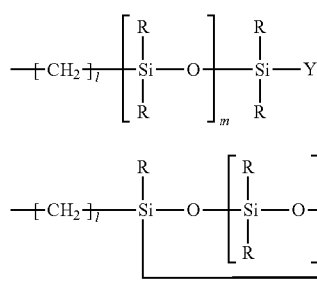

wherein l is an integer of 2 or larger; m is an integer of 0 or larger; n is an integer of 2 or larger; Y is hydrogen, alkenyl, alkyl, aryl, or a moiety bonded to a polyhedral polysiloxane via an alkylene chain, and Ys may be the same as or different from one another; Z is hydrogen, alkenyl, alkyl, aryl, or a moiety bonded to a polyhedral polysiloxane via an alkylene chain, and Zs may be the same as or different from one another, provided that at least one of Ys and Zs is hydrogen, and at least one of Ys and Zs has a structure represented by the formula (3):

$$\text{—}[CH_2]_l\text{—}R^5 \quad (3)$$

wherein l is an integer of 2 or larger, and $R^5$ is a group containing an organic silicon compound; and R is alkyl or aryl.

(10) The modified polyhedral polysiloxane of (9), wherein $R^5$ has at least one aryl group.

(11) The modified polyhedral polysiloxane of (10), wherein the aryl group is directly bonded to a silicon atom.

(12) The modified polyhedral polysiloxane of any of (1) to (11), wherein the modified polyhedral polysiloxane has at least three hydrosilyl groups on average per molecule.

(13) A polyhedral polysiloxane composition, containing the modified polyhedral polysiloxane (A) of any of (1) to (12).

(14) The polyhedral polysiloxane composition of (13), further containing a compound (B) having at least two alkenyl groups per molecule.

(15) The polyhedral polysiloxane composition of (14), wherein the compound (B) is a polysiloxane (B1) having at least two alkenyl groups per molecule.

(16) The polyhedral polysiloxane composition of (15), wherein the polysiloxane (B1) having at least two alkenyl groups per molecule has at least one aryl group.

(17) The polyhedral polysiloxane composition of (14), wherein the compound (B) is an organic compound (B2) represented by the following formula (4) and having at least two alkenyl groups per molecule:

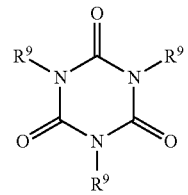

wherein $R^9$s each represent a monovalent $C_{1-50}$ organic group or hydrogen, and may be the same as or different from one another.

(18) The polyhedral polysiloxane composition of (17), wherein the organic compound (B2) has a number average molecular weight of less than 900.

(19) The polyhedral polysiloxane composition of (17) or (18), wherein the organic compound (B2) is at least one selected from the group consisting of triallyl isocyanurate, diallyl isocyanurate, diallyl monomethyl isocyanurate, and diallyl monoglycidyl isocyanurate.

(20) The polyhedral polysiloxane composition of (17) or (18), wherein the organic compound (B2) is diallyl monomethyl isocyanurate.

(21) The polyhedral polysiloxane composition of any of (13) to (20), which has a viscosity at 23° C. of not less than 1 Pa·s.

(22) The polyhedral polysiloxane composition of any of (13) to (21), containing a hydrosilylation catalyst.

(23) The polyhedral polysiloxane composition of any of (13) to (22), containing a cure retardant.

(24) A cured product, obtained by curing the polyhedral polysiloxane composition of any of (13) to (23).

(25) An optical semiconductor device, including the polyhedral polysiloxane composition of any of (13) to (23) as an encapsulant.

Advantageous Effects of Invention

The present invention provides a polyhedral polysiloxane composition that has high heat resistance and high light resistance, is excellent in gas-barrier properties and thermal shock resistance, and exhibits good handleability when used to encapsulate an optical semiconductor device.

The present invention also provides a modified polyhedral polysiloxane that is suitable as a component of a polyhedral polysiloxane composition having the above properties.

The present invention further provides a cured product that has high heat resistance and high light resistance, and is excellent in gas-barrier properties and thermal shock resistance, and an optical semiconductor device including an encapsulant having these properties.

DESCRIPTION OF EMBODIMENTS

The following description is offered to illustrate the present invention in detail.

First, the modified polyhedral polysiloxane of the present invention is described.

The modified polyhedral polysiloxane of the present invention is a modified polyhedral polysiloxane obtained by hydrosilylation of an alkenyl group-containing polyhedral polysiloxane compound (a) and a hydrosilyl group-containing compound (b), and has a structure derived from an organic silicon compound (a') having one alkenyl group per molecule.

<Alkenyl Group-Containing Polyhedral Polysiloxane Compound (a)>

The alkenyl group-containing polyhedral polysiloxane compound (a) used in the present invention is not particularly limited, provided that it is a polyhedral polysiloxane containing an alkenyl group in its molecule. Preferred specific examples include alkenyl group-containing polyhedral polysiloxane compounds that contain siloxane units represented by the formula:

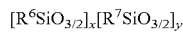

[R$^6$SiO$_{3/2}$]$_x$[R$^7$SiO$_{3/2}$]$_y$ wherein x+y is an integer of 6 to 24, provided that x is an integer of 1 or larger and y is an integer of 0 or 1 or larger; R$^6$ is an alkenyl group or a group containing an alkenyl group; and R$^7$ is any organic group or a group bonded to another polyhedral polysiloxane. Other preferred examples include alkenyl group-containing polyhedral polysiloxane compounds that contain siloxane units represented by the formula:

[AR$^1_2$SiO—SiO$_{3/2}$]$_a$[R$^2_3$SiO—SiO$_{3/2}$]$_b$ wherein a+b is an integer of 6 to 24, provided that a is an integer of 1 or larger and b is an integer of 0 or 1 or larger; A is alkenyl; R$^1$ is alkyl or aryl; and R$^2$ is hydrogen, alkyl, aryl or a group bonded to another polyhedral polysiloxane.

Examples of alkenyl groups include vinyl, allyl, butenyl, and hexenyl. In terms of the heat resistance and light resistance, vinyl is preferred.

R$^1$ is alkyl or aryl. Specific examples of alkyl groups include methyl, ethyl, propyl, butyl, cyclohexyl, and cyclopentyl, and specific examples of aryl groups include phenyl and tolyl.

In the present invention, R$^1$ is preferably methyl in terms of the heat resistance and light resistance.

R$^2$ is hydrogen, alkyl, aryl, or a group bonded to another polyhedral polysiloxane. Specific examples of alkyl groups include methyl, ethyl, propyl, butyl, cyclohexyl, and cyclopentyl, and specific examples of aryl groups include phenyl and tolyl. In the present invention, R$^2$ is preferably methyl in terms of the heat resistance and light resistance.

The symbol a is not particularly limited, provided that it is an integer of 1 or larger. In terms of the handleability of the compound and the physical properties of cured products to be obtained, a is preferably 2 or larger, and more preferably 3 or larger. Also, the symbol b is not particularly limited, provided that it is an integer of 0 or 1 or larger.

The sum of a and b (=a+b) is an integer of 6 to 24, and is preferably 6 to 12, and more preferably 6 to 10, in terms of the stability of the compound and the stability of cured products to be obtained.

The component (a) can be synthesized by any known methods without particular limitation. An exemplary synthesis method is hydrolysis-condensation of a silane compound represented by the formula: R$^8$SiX$^a_3$ wherein R$^8$ represents R$^6$ or R$^7$ described above, and X$^a$ represents halogen or a hydrolyzable functional group such as an alkoxy group. Also known is a method for synthesizing a polyhedral polysiloxane which involves synthesizing a trisilanol compound that has three silanol groups per molecule by hydrolysis-condensation of a compound of R$^8$SiX$^a_3$, and then reacting the trisilanol compound with a trifunctional silane compound that is the same as or different from the former to form a closed ring.

Still another example is hydrolysis-condensation of a tetraalkoxysilane such as tetraethoxysilane in the presence of a base such as a quaternary ammonium hydroxide. In this synthesis method, the hydrolysis-condensation of a tetraalkoxysilane produces a polyhedral silicate, and the resulting silicate is further reacted with a silylating agent such as an alkenyl group-containing silyl chloride to provide a polyhedral polysiloxane in which Si atoms forming a polyhedral structure and an alkenyl group are bonded via siloxane bonds. In the present invention, the tetraalkoxysilane may be replaced by silica or a material containing silica such as rice husk to produce a similar polyhedral polysiloxane.

<Organic Silicon Compound (a') Having One Alkenyl Group per Molecule>

The organic silicon compound (a') having one alkenyl group per molecule in the present invention reacts with the hydrosilyl group of the hydrosilyl group-containing compound (b). The use of the component (a') reduces the elastic modulus of cured products to be obtained and improves the thermal shock resistance.

Additionally, its use makes it possible to control the viscosity of compositions to be obtained. For example, when the compositions are used as encapsulants for LEDs, it is possible to inhibit phosphors from settling.

Examples of the alkenyl group include vinyl, allyl, butenyl, and hexenyl. In terms of the heat resistance and light resistance, vinyl is preferred.

The component (a') in the present invention is not particularly limited as long as it is an organic silicon compound having one alkenyl group per molecule. In terms of the gas-barrier properties and refractive index, the component (a') preferably has at least one aryl group per molecule. More preferably, in terms of the heat resistance and light resistance, the aryl group is directly bonded to a silicon atom.

The component (a') in the present invention is preferably a silane or a polysiloxane in terms of the heat resistance and light resistance. Specific examples of silanes having one alkenyl group per molecule as the component (a') include trimethylvinylsilane, dimethylphenylvinylsilane, methyldiphenylvinylsilane, triphenylvinylsilane, triethylvinylsilane, diethylphenylvinylsilane, ethyldiphenylvinylsilane, allyltrimethylsilane, allyldimethylphenylsilane, allylmethyldiphenylsilane, allyltriphenylsilane, allyltriethylsilane, allyldiethylphenylsilane, and allylethyldiphenylsilane. In particular, in terms of the heat resistance and light resistance, preferred examples include trimethylvinylsilane, dimethylphenylvinylsilane, methyldiphenylvinylsilane, and triphenylvinylsilane; and in terms of the gas-barrier properties and refractive index, preferred examples include dimethylphenylvinylsilane, methyldiphenylvinylsilane, and triphenylvinylsilane.

In the case where the component (a') is a polysiloxane, mention may be made of linear polysiloxanes having one alkenyl group, polysiloxanes having one alkenyl group at a molecular end, and cyclic siloxanes having one alkenyl group.

Specific examples of linear polysiloxanes having one alkenyl group as the component (a') include polydimethylsiloxanes whose ends are terminated with one dimethylvinylsilyl group and one trimethylsilyl group, respectively, polymethylphenylsiloxanes whose ends are terminated with one dimethylvinylsilyl group and one trimethylsilyl group, respectively, polydiphenylsiloxanes whose ends are terminated with one dimethylvinylsilyl group and one trimethylsilyl group, respectively, copolymers containing dimethylsiloxane units and methylphenylsiloxane units of which ends are terminated with one dimethylvinylsilyl group and one trimethylsilyl group, respectively, copolymers containing dimethylsiloxane units and diphenylsiloxane units of which ends are terminated with one dimethylvinylsilyl group and one trimethylsilyl group, respectively, and copolymers containing methylphenylsiloxane units and diphenylsiloxane units of which ends are terminated with one dimethylvinylsilyl group and one trimethylsilyl group, respectively.

Specific examples of polysiloxanes having one alkenyl group at a molecular end include polysiloxanes whose ends are terminated with one dimethylvinylsilyl group and one trimethylsilyl group, respectively, as mentioned above, and polysiloxanes containing one dimethylvinylsiloxane unit and at least one siloxane unit selected from the group consisting of $SiO_2$ unit, $SiO_{3/2}$ unit, SiO unit, and $SiO_{1/2}$ unit.

Specific examples of cyclic siloxanes having one alkenyl group as the component (a') include 1-vinyl-1,3,3,5,5,7,7-heptamethylcyclotetrasiloxane, 1-vinyl-3-phenyl-1,3,5,5,7,7-hexamethylcyclotetrasiloxane, 1-vinyl-3,5-diphenyl-1,3,5,7,7-pentamethylcyclotetrasiloxane, and 1-vinyl-3,5,7-triphenyl-1,3,5,7-tetramethylcyclotetrasiloxane.

Any of these organic silicon compounds having one alkenyl group per molecule as the component (a') may be used alone, or two or more of these may be used in combination.

<Hydrosilyl Group-Containing Compound (b)>

The hydrosilyl group-containing compound (b) used in the present invention is not particularly limited, provided that it has at least one hydrosilyl group per molecule. In terms of the transparency of the resulting modified polyhedral polysiloxane, the heat resistance, and light resistance, the compound (b) is preferably a hydrosilyl group-containing siloxane compound, and more preferably a hydrosilyl group-containing cyclic siloxane or a hydrosilyl group-containing linear polysiloxane. In particular, it is preferably a cyclic siloxane in terms of the heat resistance, light resistance, blue laser resistance, and gas-barrier properties.

Examples of the hydrosilyl group-containing linear polysiloxane include copolymers containing dimethylsiloxane units, methylhydrogensiloxane units, and terminal trimethylsiloxy units; copolymers containing diphenylsiloxane units, methylhydrogensiloxane units, and terminal trimethylsiloxy units; copolymers containing methylphenylsiloxane units, methylhydrogensiloxane units, and terminal trimethylsiloxy units; dimethylhydrogensilyl group-terminated polydimethylsiloxanes; dimethylhydrogensilyl group-terminated polydiphenylsiloxanes; and dimethylhydrogensilyl group-terminated polymethylphenylsiloxanes.

In particular, in terms of the reactivity in modification, the heat resistance and light resistance of cured products to be obtained, and the like, dimethylhydrogensilyl group-terminated polysiloxanes, more preferably, dimethylhydrogensilyl group-terminated polydimethylsiloxanes can be suitably used as the hydrosilyl group-containing linear polysiloxane. Preferred specific examples include tetramethyldisiloxane and hexamethyltrisiloxane.

Examples of the hydrosilyl group-containing cyclic siloxane include 1,3,5,7-tetrahydrogen-1,3,5,7-tetramethylcyclotetrasiloxane, 1-propyl-3,5,7-trihydrogen-1,3,5,7-tetramethylcyclotetrasiloxane, 1,5-dihydrogen-3,7-dihexyl-1,3,5,7-tetramethylcyclotetrasiloxane, 1,3,5-trihydrogen-1,3,5-trimethylcyclotrisiloxane, 1,3,5,7,9-pentahydrogen-1,3,5,7,9-pentamethylcyclopentasiloxane, and 1,3,5,7,9,11-hexahydrogen-1,3,5,7,9,11-hexamethylcyclohexasiloxane.

In the present invention, specifically, for example, 1,3,5,7-tetrahydrogen-1,3,5,7-tetramethylcyclotetrasiloxane is suitable as the cyclic siloxane in terms of the industrial availability and reactivity, the heat resistance, light resistance, and strength of cured products to be obtained, and the like.

Any of these hydrosilyl group-containing compounds as the component (b) may be used alone, or two or more of these may be used in combination.

<Modified Polyhedral Polysiloxane>

The modified polyhedral polysiloxane of the present invention can be obtained by hydrosilylation of an alkenyl group-containing polyhedral polysiloxane compound (a) and an organic silicon compound (a') having one alkenyl group per molecule with a hydrosilyl group-containing compound (b) in the presence of a later-described hydrosilylation catalyst.

Various methods can be used without particular limitation to produce the modified polyhedral polysiloxane of the present invention. The component (a) and the component (b) may be reacted first, followed by reaction with the component (a'), or the component (a') and the component (b) may be reacted first, followed by reaction with the component (a). Alternatively, the component (a) and the component (a') may be simultaneously reacted with the component (b). After each reaction step, volatile unreacted components may be evaporated, for example, under reduced pressure and heating, to obtain the target product or an intermediate for a subsequent step. In order to reduce the formation of the compound free from the component (a) resulting from only the reaction of the component (a') and the component (b), it is preferable that the component (a) and the component (b) be reacted, followed by evaporation of the unreacted component (b) and then reaction with the component (a'). In terms of the heat resistance, it is preferable to reduce the formation of the compound free from the component (a) resulting from only the reaction of the component (a') and the component (b).

Part of alkenyl groups from the component (a) used in the reaction may be left in the modified polyhedral polysiloxane thus obtained.

The amount of the component (b) is preferably determined so that the number of hydrosilyl groups is 2.5 to 20 per alkenyl group of the component (a). If the amount is small, then the cross-linking reaction accelerates gelation, possibly resulting in a modified polyhedral polysiloxane with poor handleability. If the amount is large, the physical properties of the cured products may be adversely affected.

The amount of the component (a') is preferably determined so that the number of alkenyl groups is 0.01 to 0.36 per hydrosilyl group of the component (b). If the amount is small, the effect of improving the thermal shock resistance of cured products to be obtained may be small, whereas if the amount is large, cured products that have been insufficiently cured may be obtained.

The amount of the hydrosilylation catalyst used in synthesis of the modified polyhedral polysiloxane is not particularly limited, and is preferably $10^{-1}$ to $10^{-10}$ mol, and more preferably $10^{-4}$ to $10^{-8}$ mol, per mol of alkenyl groups of the components (a) and (a') used in the reaction. Since some hydrosilylation catalysts absorb light with short wavelengths, the use of a large amount of hydrosilylation catalyst may cause coloring. Additionally, then cured products to be obtained may have reduced light resistance and may be foamed. The use of a small amount of hydrosilylation catalyst may not allow the reaction to proceed, and thus the target product may not be provided.

The reaction temperature of the hydrosilylation is about 30 to 400° C. and is preferably 40 to 250° C., more preferably 45 to 140° C. At too low temperatures, the reaction may not proceed to a sufficient extent, whereas at too high temperatures, gelation may occur leading to poor handleability.

The modified polyhedral polysiloxane of the present invention may be a polyhedral polysiloxane compound containing a siloxane unit represented by the formula:

wherein a+b is an integer of 6 to 24, provided that a is an integer of 1 or larger and b is an integer of 0 or 1 or larger; $R^3$ is alkyl or aryl; $R^4$ is alkenyl, hydrogen, alkyl, aryl, or a group bonded to another polyhedral polysiloxane; and X has a structure represented by the following formula (1) or (2), and in the case where multiple Xs are present, the structures of the formula (1) or (2) may be different from one another and the structures of the formulas (1) and (2) may coexist:

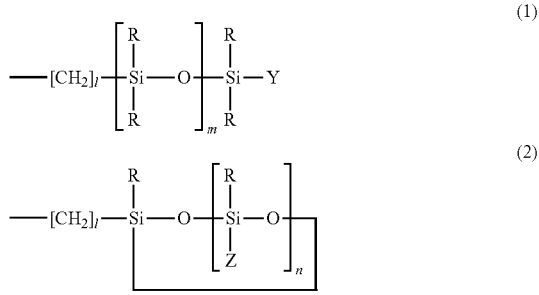

wherein l is an integer of 2 or larger; m is an integer of 0 or larger; n is an integer of 2 or larger; Y is hydrogen, alkenyl, alkyl, aryl, or a moiety bonded to a polyhedral polysiloxane via an alkylene chain, and Ys may be the same as or different from one another; Z is hydrogen, alkenyl, alkyl, aryl, or a moiety bonded to a polyhedral polysiloxane via an alkylene chain, and Zs may be the same as or different from one another, provided that at least one of Ys and Zs is hydrogen, and at least one of Ys and Zs has a structure represented by the formula (3):

wherein l is an integer of 2 or larger, and $R^5$ is a group containing an organic silicon compound; and R is alkyl or aryl.

Here, $R^5$ is not particularly limited as long as it is a group containing a silicon compound. In terms of the gas-barrier properties and refractive index, $R^5$ preferably has at least one aryl group per molecule. More preferably, in terms of the heat resistance and light resistance, the aryl group is directly bonded to a silicon atom.

The above-described modified polyhedral polysiloxane of the present invention certainly has compatibility with various compounds, specifically with the later-described component (B). Additionally, due to the presence of the hydrosilyl group in its molecule, it can react with various alkenyl group-containing compounds. More specifically, it can react with a polysiloxane (B1) or organic compound (B2) having at least two alkenyl groups per molecule mentioned later to give a cured product having excellent heat resistance, light resistance, blue laser resistance, and gas-barrier properties.

The modified polyhedral polysiloxane of the present invention can be prepared in liquid form at 20° C. The modified polyhedral polysiloxane in liquid form is preferred because it is easy to handle.

In terms of the strength, heat resistance, light resistance, and gas-barrier properties of cured products to be obtained, the modified polyhedral polysiloxane of the present invention preferably has at least three hydrosilyl groups on average per molecule.

Next, the polyhedral polysiloxane composition of the present invention is described.

The polyhedral polysiloxane composition of the present invention is characterized by containing the above-described modified polyhedral polysiloxane of the present invention (hereinafter, also referred to as modified polyhedral polysiloxane (A)), and may further contain a compound (B) having at least two alkenyl groups per molecule.

In the case where the polyhedral polysiloxane composition of the present invention contains the compound (B), the composition is cured into a cured product as a result of hydrosilylation of the alkenyl group of the compound (B) with the hydrosilyl group of the modified polyhedral polysiloxane (A). The hydrosilylation is preferably performed in the presence of a hydrosilylation catalyst.

Examples of hydrosilylation catalysts usable in this reaction are mentioned later.

It is not necessary to additionally use any hydrosilylation catalyst for hydrosilylation of the modified polyhedral polysiloxane (A) and the compound (B) because the modified polyhedral polysiloxane carries the hydrosilylation catalyst used in synthesis of the modified polyhedral polysiloxane (A).

The amount of the compound (B) can be determined as desired, and the compound (B) is preferably added so that the number of hydrosilyl groups of the modified polyhedral polysiloxane (A) is 0.3 to 5, more preferably 0.5 to 3, per alkenyl group. If the ratio of alkenyl groups is too small, a poor appearance due to foaming or the like is likely to be caused. Also, if the ratio of alkenyl groups is too large, the physical properties after curing may be adversely affected.

For example, the compound (B) is preferably a polysiloxane (B1) having at least two alkenyl groups per molecule, a later-described organic compound (B2), or the like. The components (B1) and (B2) may be used in combination.

<Polysiloxane (B1) Having at Least Two Alkenyl Groups per Molecule>

In the present invention, the number of siloxane units in the polysiloxane (B1) having at least two alkenyl groups per molecule is not particularly limited, and is preferably not less than 2, and more preferably 2 to 10. If the number of siloxane units per molecule is small, then the polysiloxane tends to evaporate easily from the composition and desired physical properties may not be obtained after curing. Also, if the number of siloxane units is large, cured products with reduced gas-barrier properties may be obtained.

In terms of the gas-barrier properties, the polysiloxane (B1) having at least two alkenyl groups per molecule preferably contains an aryl group. In terms of the heat resistance and light resistance, the aryl group of the aryl group-containing polysiloxane having at least two alkenyl groups per molecule is preferably bonded directly to an Si atom. Moreover, the aryl group may be located either in a side chain or at an end of the molecule. The molecular structure of the aryl group-containing polysiloxane is not limited and may be, for example, a linear structure, a branched structure, a partially branched linear structure, or a cyclic structure.

Examples of the aryl group include phenyl, naphthyl, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 3-isopropylphenyl, 4-isopropylphenyl, 2-butylphenyl, 3-butylphenyl, 4-butylphenyl, 3-isobutylphenyl, 4-isobutylphenyl, 3-t-butylphenyl, 4-t-butylphenyl, 3-pentylphenyl, 4-pentylphenyl, 3-hexylphenyl, 4-hexylphenyl, 3-cyclohexylphenyl, 4-cyclohexylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3-diethylphenyl, 2,4-diethylphenyl, 2,5-diethylphenyl, 2,6-diethylphenyl, 3,4-diethylphenyl, 3,5-diethylphenyl, biphenyl, 2,3,4-trimethylphenyl, 2,3,5-trimethylphenyl, 2,4,5-trimethylphenyl, 3-epoxyphenyl, 4-epoxyphenyl, 3-glycidylphenyl, and 4-glycidylphenyl. In particular, in terms of the heat and light resistance, phenyl is preferred. Any of these may be used alone, or two or more of these may be used in combination.

In terms of the heat resistance and light resistance, preferred examples of the polysiloxane (B1) having at least two alkenyl groups per molecule include linear polysiloxanes having at least two alkenyl groups, polysiloxanes having at least two alkenyl groups at molecular end(s), and cyclic siloxanes having at least two alkenyl groups.

Specific examples of the linear polysiloxanes having at least two alkenyl groups include copolymers containing dimethylsiloxane units, methylvinylsiloxane units, and terminal trimethylsiloxy units; copolymers containing diphenylsiloxane units, methylvinylsiloxane units, and terminal trimethylsiloxy units; copolymers containing methylphenylsiloxane units, methylvinylsiloxane units, and terminal trimethylsiloxy units; dimethylvinylsilyl group-terminated polydimethylsiloxanes; dimethylvinylsilyl group-terminated polydiphenylsiloxanes; and dimethylvinylsilyl group-terminated polymethylphenylsiloxanes.

Specific examples of the polysiloxanes having at least two alkenyl groups at molecular end(s) include dimethylvinylsilyl group-terminated polysiloxanes mentioned above; and polysiloxanes containing two or more dimethylvinylsiloxane units and at least one siloxane unit selected from the group consisting of $SiO_2$ unit, $SiO_{3/2}$ unit, and SiO unit.

Examples of the cyclic siloxane compounds having at least two alkenyl groups include 1,3,5,7-vinyl-1,3,5,7-tetramethylcyclotetrasiloxane, 1,3,5,7-vinyl-1-phenyl-3,5,7-trimethylcyclotetrasiloxane, 1,3,5,7-vinyl-1,3-diphenyl-5,7-dimethylcyclotetrasiloxane, 1,3,5,7-vinyl-1,5-diphenyl-3,7-dimethylcyclotetrasiloxane, 1,3,5,7-vinyl-1,3,5-triphenyl-7-methylcyclotetrasiloxane, 1-phenyl-3,5,7-trivinyl-1,3,5,7-tetramethylcyclotetrasiloxane, 1,3-diphenyl-5,7-divinyl-1,3,5,7-tetramethylcyclotetrasiloxane, 1,3,5-trivinyl-1,3,5-trimethylcyclosiloxane, 1,3,5,7,9-pentavinyl-1,3,5,7,9-pentamethylcyclosiloxane, and 1,3,5,7,9,11-hexavinyl-1,3,5,7,9,11-hexamethylcyclosiloxane.

Any of these polysiloxanes (B1) having at least two alkenyl groups per molecule may be used alone, or two or more of these may be used in combination.

<Organic Compound (B2)>

Specifically, for example, the component (B2) in the present invention functions as a crosslinker for the component (A) to provide a cured product having heat resistance, light resistance, and gas-barrier properties.

The organic compound (B2) in the present invention is not particularly limited as long as it is an organic compound represented by the formula (4) below and having at least two alkenyl groups per molecule.

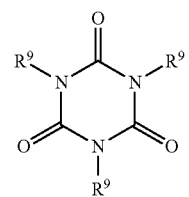

(4)

In the formula, $R^9$s each represent a monovalent $C_{1-50}$ organic group or hydrogen, and may be the same as or different from one another.

The presence of at least two alkenyl groups in each molecule of the component (B2) in the present invention contributes to excellent properties (e.g. strength, gas-barrier properties, heat resistance, light resistance) of cured products to be obtained. In terms of the gas-barrier properties, the component (B2) preferably has a number average molecular weight of less than 900.

The component (B2) is preferably an isocyanuric acid derivative represented by the above formula (4) and having at least two alkenyl groups per molecule in terms of, for example, the adhesion between a substrate and the composition cured thereon, and is more preferably triallyl isocyanurate, diallyl isocyanurate, diallyl monomethyl isocyanurate, or diallyl monoglycidyl isocyanurate in terms of the balance of the heat resistance and light resistance. In particular, diallyl monomethyl isocyanurate is still more preferred in terms of the thermal shock resistance.

The component (B2) may contain a functional group other than alkenyl groups in its structure. In terms of the compatibility with the component (A), preferred are low polar functional groups such as linear aliphatic hydrocarbon groups (e.g. methyl, ethyl, propyl). In particular, methyl is preferred in terms of the heat resistance and light resistance.

<Hydrosilylation Catalyst>

In the present invention, a hydrosilylation catalyst is used in synthesis of the modified polyhedral polysiloxane (A) and in curing of the polyhedral polysiloxane composition containing the modified product (A).

In the present invention, any of generally known hydrosilylation catalysts can be used without particular limitation.

Specific examples thereof include platinum-olefin complexes, chloroplatinic acid, elemental platinum, and carriers (such as alumina, silica, and carbon black) which carry solid platinum; platinum-vinylsiloxane complexes such as $Pt_n(ViMe_2SiOSiMe_2Vi)_n$ and $Pt[(MeViSiO)_4]_m$; platinum-phosphine complexes such as $Pt(PPh_3)_4$ and $Pt(PBu_3)_4$; platinum-phosphite complexes such as $Pt[P(OPh)_3]_4$ and $Pt[P(OBu)_3]_4$ in which Me represents methyl, Bu represents butyl, Vi represents vinyl, Ph represents phenyl, and n and m each represent an integer; and Pt(acac)$_2$. In addition, platinum-hydrocarbon complexes as disclosed in U.S. Pat. No. 3,159,601 and U.S. Pat. No. 3,159,662 by Ashby et al., and platinum alcoholate catalysts as disclosed in U.S. Pat. No. 3,220,972 by Lamoreaux et al. may also be mentioned.

Examples of the catalysts other than platinum compounds include RhCl(PPh$_3$)$_3$, RhCl$_3$, Rh/Al$_2$O$_3$, RiCl$_3$, IrCl$_3$, FeCl$_3$, AlCl$_3$, PdCl$_2$.2H$_2$O, NiCl$_2$, and TiCl$_4$. The catalysts may be used alone, or two or more of them may be used in combination. In terms of catalytic activity, preferred are chloroplatinic acid, platinum-olefin complexes, platinum-vinylsiloxane complexes, Pt(acac)$_2$, and the like.

<Cure Retardant>

A cure retardant is a component to improve the storage stability of the polyhedral polysiloxane composition of the present invention or to control the reactivity in hydrosilylation in the curing process. In the present invention, the cure retardant used may be any one generally known to be used for addition-curable compositions curable in the presence of a hydrosilylation catalyst, and specific examples thereof include compounds containing an aliphatic unsaturated bond, organophosphorus compounds, organosulfur compounds, nitrogen-containing compounds, tin compounds, and organic peroxides. Any of these may be used alone, or two or more of these may be used in combination.

Specific examples of the compounds containing an aliphatic unsaturated bond include propargyl alcohols such as 3-hydroxy-3-methyl-1-butyne, 3-hydroxy-3-phenyl-1-butyne, 3,5-dimethyl-1-hexyn-3-ol, and 1-ethynyl-1-cyclohexanol; ene-yne compounds; and maleic anhydride and maleates such as dimethyl maleate.

Specific examples of the organophosphorus compounds include triorganophosphines, diorganophosphines, organophosphones, and triorganophosphites.

Specific examples of the organosulfur compounds include organomercaptans, diorganosulfides, hydrogen sulfide, benzothiazole, thiazole, and benzothiazole disulfide.

Specific examples of the nitrogen-containing compounds include N,N,N',N'-tetramethylethylenediamine, N,N-dimethylethylenediamine, N,N-diethylethylenediamine, N,N-dibutylethylenediamine, N,N-dibutyl-1,3-propanediamine, N,N-dimethyl-1,3-propanediamine, N,N,N',N'-tetraethylethylenediamine, N,N-dibutyl-1,4-butanediamine, and 2,2'-bipyridine.

Specific examples of the tin compounds include stannous halide dihydrates and stannous carboxylates.

Specific examples of the organic peroxides include di-t-butyl peroxide, dicumyl peroxide, benzoyl peroxide, and t-butyl perbenzoate. Among the above-mentioned examples, dimethyl maleate, 3,5-dimethyl-1-hexyn-3-ol, and 1-ethynyl-1-cyclohexanol may be mentioned as particularly preferred cure retardants.

The amount of the cure retardant is not particularly limited, and it preferably ranges from $10^{-1}$ to $10^3$ mol, more preferably from 1 to 300 mol, and still more preferably from 1 to 100 mol, per mol of the hydrosilylation catalyst. Any of these cure retardants may be used alone, or two or more of these may be used in combination.

<Polyhedral Polysiloxane Composition>

The polyhedral polysiloxane composition of the present invention can be prepared by mixing the components (A) and (B), and optionally other components such as the above-described hydrosilylation catalyst and cure retardant. The polyhedral polysiloxane composition of the present invention can be prepared and handled as a liquid resin composition. The liquid resin composition can be injected into or applied to a mold, package, substrate, or the like and then cured to easily provide a molded product suited for the intended use.

Moreover, the polyhedral polysiloxane composition of the present invention preferably has a viscosity at 23° C. of not less than 1 Pa·s. This is because the composition exhibits better handleability when used to encapsulate an optical semiconductor device or the like.

In the case where the polyhedral polysiloxane composition is cured by heating, the temperature is preferably selected from 30 to 400° C., and more preferably 50 to 250° C. At too high curing temperatures, cured products with poor appearance tend to be obtained, whereas at too low curing temperatures, the curing may not proceed to a sufficient extent. The composition may be cured using a two-step or multi-step temperature profile. More specifically, for example, the curing temperature may preferably be stepwise raised, for example, to 70° C., then to 120° C., and then to 150° C. because satisfactory cured products can be obtained.

The curing period can be appropriately determined according to the curing temperature, the amount of the hydrosilylation catalyst used, and the amount of reactive groups, as well as the combination of other components in the polyhedral polysiloxane composition. By way of example only, a curing period of one minute to 12 hours, preferably of 10 minutes to 8 hours, leads to production of satisfactory cured products.

Cured products obtained by curing the polyhedral polysiloxane composition of the present invention are another aspect of the present invention.

The polyhedral polysiloxane composition of the present invention may optionally contain an adhesion promoter.

The adhesion promoter is a component used, for example, to enhance adhesion between the polyhedral polysiloxane composition of the present invention and a substrate. There is no limitation in selecting the adhesion promoter as long as it exerts such an effect, and preferred examples thereof include silane coupling agents.

The silane coupling agents are not particularly limited as long as they are compounds each of which has at least one functional group reactive with an organic group, and at least one hydrolyzable silyl group per molecule. The functional group reactive with an organic group is preferably at least one functional group selected from the group consisting of epoxy, methacrylic, acrylic, isocyanate, isocyanurate, vinyl, and carbamate groups, in terms of the handleability. In terms of the curability and adhesion, epoxy, methacrylic, and acrylic groups are particularly preferred. The hydrolyzable silyl group is preferably an alkoxysilyl group in terms of the handleability, and in particular, methoxysilyl and ethoxysilyl groups are preferred in terms of the reactivity.

Preferred specific examples of the silane coupling agents include alkoxysilanes containing an epoxy functional group, such as 3-glycidoxypropyltrimethoxysilane, 3-glycidoxypropylmethyldimethoxysilane, 3-glycidoxypropyltriethoxysilane, 3-glycidoxypropylmethyldiethoxysilane, 2-(3,4-epoxycyclohexyl)ethyltrimethoxysilane, 2-(3,4-epoxycyclohexyl)ethylmethyldimethoxysilane, 2-(3,4-epoxycyclohexyl)ethyltriethoxysilane, and 2-(3,4-epoxycyclohexyl)ethylmethyldiethoxysilane; and alkoxysilanes containing a methacrylic or acrylic group, such as 3-methacryloxypropyltrimethoxysilane, 3-methacryloxypropyltriethoxysilane, 3-acryloxypropyltrimethoxysilane, 3-acryloxypropyltriethoxysilane, methacryloxymethyltrimethoxysilane, methacryloxymethyltriethoxysilane, acryloxymethyltrimethoxysilane, and acryloxymethyltriethoxysilane. Any of these may be used alone, and two or more of these may be used in combination.

The amount of the silane coupling agent is preferably 0.05 to 30 parts by weight, and more preferably 0.1 to 10 parts by weight, for each 100 parts by weight of a mixture of the components (A) and (B). If the amount is small, the effect of improving adhesion may not be obtained. If the amount is large, the physical properties of the cured products may be adversely affected.

In the present invention, a known adhesion enhancer may also be used in order to enhance the effect of the adhesion promoter. Examples of the adhesion enhancer include, but are not limited to, epoxy-containing compounds, epoxy resins, boronic acid ester compounds, organoaluminum compounds, and organotitanium compounds.

The polyhedral polysiloxane composition of the present invention may optionally contain an inorganic filler.

The use of an inorganic filler can improve the physical properties of molded products to be obtained, in terms of the strength, hardness, elastic modulus, coefficient of thermal expansion, thermal conductivity, heat dissipation, electrical characteristics, light reflectance, flame retardancy, fire resistance, gas-barrier properties, and the like.

The inorganic filler is not particularly limited as long as it is an inorganic material or a compound that contains an inorganic material, and specific examples thereof include silica-based inorganic fillers (e.g. quartz, fumed silica, precipitated silica, silicic anhydride, molten silica, crystalline silica, ultrafine amorphous silica), alumina, zircon, iron oxide, zinc oxide, titanium oxide, silicon nitride, boron nitride, aluminum nitride, silicon carbide, glass fiber, glass flakes, alumina fiber, carbon fiber, mica, black lead, carbon black, ferrite, graphite, diatomaceous earth, white clay, clay, talc, aluminum hydroxide, calcium carbonate, manganese carbonate, magnesium carbonate, barium sulfate, potassium titanate, calcium silicate, inorganic balloons, and silver powder. Any of these may be used alone, or two or more of these may be used in combination.

The inorganic filler may appropriately be surface-treated. Examples of the surface treatment include, but are not limited to, alkylation treatment, trimethylsilylation treatment, silicone treatment, and treatment with a silane coupling agent.

Inorganic fillers having various shapes such as crushed, flake, spherical, and rod shapes may be used. The average particle size and particle size distribution of the inorganic filler are not particularly limited, and the preferred average particle size ranges from 0.005 to 50 µm, more preferably from 0.01 to 20 µm, in terms of the gas-barrier properties. The BET specific surface area thereof is not particularly limited either, and it is preferably not less than 70 $m^2/g$, more preferably not less than 100 $m^2/g$, and particularly preferably not less than 200 $m^2/g$, in terms of the gas-barrier properties.

The amount of the inorganic filler added is not particularly limited, and is preferably 1 to 1000 parts by weight, more preferably 3 to 500 parts by weight, and still more preferably 5 to 300 parts by weight, for each 100 parts by weight of the mixture of the components (A) and (B). A large amount of inorganic filler added may reduce the fluidity of the composition, whereas a small amount of inorganic filler may not provide desired physical properties.

The order of mixing of the inorganic filler is not particularly limited. A preferred order in terms of better storage stability is mixing the inorganic filler with the component (B) followed by mixing with the component (A). Another preferred order is mixing the inorganic filler with a mixture of the components (A) and (B) because the reaction components, namely, the components (A) and (B) are well mixed so that stable molded products tend to be obtained.

The means for mixing the inorganic filler is not particularly limited, and specific examples thereof include stirring apparatus such as two-roll or three-roll mills, planetary stirring and defoaming apparatus, homogenizers, dissolvers, and planetary mixers, and melt-kneaders such as plastomill. The inorganic filler may be mixed at ordinary temperature or under heated conditions, and may be mixed at ordinary pressure or under vacuum conditions. If the inorganic filler is mixed at elevated temperatures, the composition may be cured before molding.

Also, the polyhedral polysiloxane composition of the present invention may optionally contain various additives (e.g. phosphors, colorants, and heat-resistance improving agents), reaction control agents, mold release agents, dispersants for fillers, and the like. Examples of the dispersants for fillers include diphenylsilanediol, various alkoxysilanes, carbon-functional silanes, and silanol group-containing siloxanes with low molecular weights. These optional components are preferably used in minimum amounts so that they do not impair the effects of the present invention.

The polyhedral polysiloxane composition of the present invention may be prepared by homogeneously mixing the above components with a kneading machine such as a roll mill, Banbury mixer, or kneader, or with a planetary stirring and defoaming apparatus, and optionally performing a heating treatment.

The polyhedral polysiloxane composition of the present invention may be converted into and used as a molded product.

The molding method may be any method such as extrusion molding, compression molding, blow molding, calender molding, vacuum molding, foam molding, injection molding, liquid injection molding, and cast molding.

Specific examples of applications of molded products to be obtained according to the present invention include, in the liquid crystal display field, peripheral materials for liquid crystal display devices such as substrate materials, light guide plates, prism sheets, polarizing plates, retardation films, viewing angle compensation films, adhesives, color filters, and films for LCDs such as polarizer protective films and passivation films. Other examples include materials for PDPs (plasma display panels), such as encapsulants, anti-reflection films, optical compensation films, housing materials, protection films for front glass, alternative materials for front glass, adhesives, color filters, and passivation films; materials for LED devices, such as molding materials for LED elements, protection films for front glass, alternative materials for front glass, adhesives, color filters, and passivation films; materials for plasma address liquid crystal displays, such as substrate materials, light guide plates, prism sheets, polarizing plates, retardation films, viewing angle compensation films, adhesives, color filters, polarizer protective films, and passivation films; materials for organic EL displays, such as protection films for front glass, alternative materials for front glass, color filters, adhesives, and passivation films; and materials for field emission displays (FEDs), such as various film substrates, protection films for front glass, alternative materials for front glass, adhesives, color filters, and passivation films.

Examples of the applications in the optical recording field include materials for VDs (video disks), CD/CD-ROMs, CD-R/RWs, DVD-R/DVD-RAMs, MO/MDs, PDs (phase-change disks), and optical cards, such as disk substrate materials, pickup lenses, protective films, encapsulants, and adhesives. More specifically, there may be mentioned materials for optical pickups of next-generation DVDs and the like, such as pickup lenses, collimator lenses, objective lenses, sensor lenses, protective films, encapsulants for elements, encapsulants for sensors, gratings, adhesives, prisms, wave plates, correcting plates, splitters, holograms, and mirrors.

Examples of the applications in the optical equipment field include materials for still cameras, such as materials for lenses, prism finders, target prisms, finder covers, and light sensors; materials for video cameras, such as taking lenses and finders; materials for projection televisions, such as projector lenses, protective films, encapsulants, and adhesives; and materials for optical sensing equipment, such as materials for lenses, encapsulants, adhesives, and films.

Examples of the applications in the optical components field include peripheral materials for optical switches in optical communication systems, such as fiber materials, lenses, waveguides, and encapsulants and adhesives for elements; peripheral materials for optical connectors, such as optical fiber materials, ferrules, encapsulants, and adhesives; materials for passive optical components and optical circuit components, such as lenses, waveguides, and encapsulants and adhesives for LED elements; and peripheral materials for opto-electronic integrated circuits (OEICs), such as substrate materials, fiber materials, and encapsulants and adhesives for elements.

Examples of the applications in the optical fiber field include materials for decoration displays, such as lighting and light guides; sensors, indications, signs and the like for industrial use; and optical fibers for communications infrastructures and for home networking of digital devices.

Examples of the applications as peripheral materials for semiconductor integrated circuits include interlayer insulators, passivation films, and resist materials for microlithography for LSI and ultra LSI materials.

Examples of the applications in the automotive and transport fields include materials for automobiles, such as lamp reflectors, bearing retainers, gear parts, corrosion-resistant coatings, switch parts, headlamps, inner parts of the engine, electrical parts, various interior and exterior parts, driving engines, brake-oil tanks, rust-proof steel plates for automobiles, interior panels, interior materials, protecting/binding wire harnesses, fuel hoses, automotive lamps, and glass substitutes. Other examples include multilayer glasses for railway vehicles. Further examples include materials for aircrafts, such as toughening agents for structural materials, peripheral members of the engine, protecting/binding wire harnesses, and corrosion-resistant coatings.

Examples of the applications in the architecture field include interior/processing materials, lamp covers, sheets, glass interlayer films, glass substitutes, and peripheral materials for solar cells. Examples in the agricultural field include cover films for greenhouses.

Examples of the applications as next generation optical/electronic functional organic materials include next-generation DVDs; peripheral materials for organic EL elements; organic photorefractive elements; light-light conversion devices such as optical amplifiers and optical computing elements; and peripheral materials for organic solar cells, such as substrate materials, fiber materials, and encapsulants and adhesives for elements.

Optical semiconductor devices including the polyhedral polysiloxane composition of the present invention as an encapsulant are also another aspect of the present invention.

EXAMPLES

The present invention is described in greater detail, referring to examples which are not to be construed as limiting the present invention.

(Viscosity)

Measured using an E-type viscometer (available from TOKYO KEIKI INC.) with a cone (EHD-type, φ48, 1-fold) at 23.0° C.

(SiH Value)

The SiH value the amount mined by mixing a tested compound with dibromoethane, dissolving the mixture in deuterated chloroform, performing NMR analysis on the solution by 300 MHz NMR (available from Varian Technologies Japan, Ltd.), and calculating the SiH value using the following equation (1):

SiH value (mol/kg)=[integrated peak value of SiH group of compound]/[integrated peak value of methyl group of dibromoethane]×4×[weight of dibromoethane in mixture]/[molecular weight of dibromoethane]/[weight of compound in mixture]   (1).

(Preparation of Sample for Heat Resistance Test and Light Resistance Test)

A polyhedral polysiloxane composition was charged into a mold and heat-cured in a convection oven for two hours at 80° C. followed by one hour at 100° C. and then five hours at 150° C. In this manner, a 2 mm-thick sample was prepared.

(Heat Resistance Test)

Each sample obtained in the manner described above was aged for 200 hours in a convection oven set at 150° C. (in air), and then visually observed.

Samples without any color change due to coloring or the like were evaluated as "good", and samples with color changes were evaluated as "bad".

(Light Resistance Test)

A metaling weather meter (model: M6T, available from Suga Test Instruments Co., Ltd.) was used. Each sample obtained in the manner described above was irradiated at a black panel temperature of 120° C. and an irradiance of 0.53 kW/m$^2$ until the total irradiance reached 50 MJ/m$^2$, and then visually observed.

Samples without any color change due to coloring or the like were evaluated as "good", and samples with color changes were evaluated as "bad".

(Preparation of Sample for Thermal Shock Test)

A single piece of single-crystal silicon chip with a size of 0.4 mm×0.4 mm×0.2 mm was bonded to an LED package (product name: TOP LED 1-IN-1, available from Enomoto Co., Ltd.) with an epoxy adhesive (product name: Loctite 348, available from Henkel Japan Ltd.), and the resulting LED package was heated for 30 minutes in a convection oven set at 150° C. so that the chip was fixed on the LED package. A polyhedral polysiloxane composition was then injected into the LED package, and then heat-cured in a convection oven for two hours at 80° C. followed by one hour at 100° C. and then five hours at 150° C. In this manner, a sample was prepared.

(Thermal Shock Test)

Each sample obtained in the manner described above was subjected to 200 cycles of high temperature exposure at 100° C. for 30 minutes and low temperature exposure at −40° C. for 30 minutes with a thermal shock tester (available from Espec Corporation, TSA-71H-W), and then observed.

Samples were evaluated as "good" when no visible change was observed after the test, and as "bad" when cracks in the resin, separation between the resin and the package, or coloring of the resin was observed.

(Preparation of Sample for Moisture Permeability Test)

In the present invention, the moisture permeability of a cured product to be obtained is used as a measure of the gas-barrier properties of the cured product. In other words, a lower moisture permeability corresponds to a higher level of gas-barrier properties.

A polyhedral polysiloxane composition was charged into a mold and heat-cured in a convection oven for two hours at 80° C. followed by one hour at 100° C. and then five hours at 150° C. In this manner, a sample (5 cm square, 2 mm thick) was prepared. This sample was aged for 24 hours at room temperature (25° C.) at a humidity of 55% RH.

(Moisture Permeability Test)

On a 5 cm-square glass plate (0.5 mm thick), a 5 cm-square polyisobutylene rubber sheet (3 mm thick, a 3-cm-square part inside the sheet had been cut out to form a hollow square) was fixed to prepare a jig. The hollow part was filled with 1 g of calcium chloride (for water content measurement, available from Wako Pure Chemical Industries, Ltd.). Further, each sample (5 cm square, 2 mm thick) obtained as above was fixed thereon to prepare a test sample. This test sample was aged in a constant temperature and humidity chamber (available from Espec Corporation, PR-2KP) at 40° C. and a humidity of 90% RH for 24 hours. The moisture permeability (water vapor permeability) was then calculated according to the following equation (2):

Moisture permeability (g/m$^2$/day)={(weight of entire test sample after moisture permeability test (g))−(weight of entire test sample before moisture permeability test (g))}×10000/9     (2)

(Hydrogen Sulfide Test)

A polyhedral polysiloxane composition was injected into an LED package (product name: TOP LED 1-IN-1, available from Enomoto Co., Ltd.) and heat-cured in a convection oven for two hours at 80° C. followed by one hour at 100° C. and then five hours at 150° C. In this manner, a sample was prepared. This sample was placed in a flow gas corrosion tester (available from Fact K Co., Ltd., KG130S) and subjected to a hydrogen sulfide exposure test for 96 hours under the conditions of 40° C., 80% RH, and 3 ppm of hydrogen sulfide.

Samples were evaluated as "good" when no color change was observed on a reflector of the package after the test, as "intermediate" when a slight color change was observed, and as "bad" when color changes were observed.

(Phosphor Settling Test)

To 5 g of a polyhedral polysiloxane composition was added 0.05 g of a phosphor (available from Intematix, Y3957), and the mixture was stirred well and then left standing still. During this time the mixture was observed every hour.

Mixtures were evaluated as "bad" when the phosphor settled within one hour, as "intermediate" when the phosphor settled in one to six hours, and as "good" when the phosphor remained dispersed even after more than six hours.

Production Example 1

Tetraethoxysilane (1083 g) was added to a 48% aqueous solution of choline (aqueous solution of trimethyl(2-hydroxyethyl)ammonium hydroxide, 1262 g), and the mixture was vigorously stirred at room temperature for two hours. When the reaction system generated heat and turned into a homogeneous solution, the stirring was slowed down and then the solution was left to react for 12 hours. Then, to a solid formed in the reaction system, methanol (1000 mL) was added to give a homogeneous solution.

The methanol solution was slowly added dropwise to a vigorously stirred solution of dimethylvinylchlorosilane (537 g), trimethylsilyl chloride (645 g), and hexane (1942 mL). After completion of the dropwise addition, the resulting mixture was left to react for one hour. Then, the organic layer was extracted and concentrated to a solid. Next, the obtained solid was washed in methanol by vigorous stirring, and filtered to yield 592 g of a white solid of tris(vinyldimethylsiloxy)-pentakis(trimethylsiloxy)octasilsesquioxane (Fw=1166.2), which was an alkenyl group-containing polyhedral polysiloxane compound with 16 Si atoms and three vinyl groups.

Example 1

A 5.00 g portion of the tris(vinyldimethylsiloxy)-pentakis(trimethylsiloxy)octasilsesquioxane (an alkenyl group-containing polyhedral polysiloxane compound) prepared in Production Example 1 was dissolved in toluene (10.0 g), and combined with a xylene solution (0.48 μL) of a platinum-vinylsiloxane complex (platinum-vinylsiloxane complex containing 3 wt % of platinum, available from Umicore Precious Metals Japan Co., Ltd., Pt-VTSC-3X). The resulting solution was slowly added dropwise to a solution of 1,3,5,7-tetrahydrogen-1,3,5,7-tetramethylcyclotetrasiloxane (3.09 g, an amount such that the number of hydrosilyl groups is 4.0 per alkenyl group of the tris(vinyldimethylsiloxy)-pentakis(trimethylsiloxy)octasilsesquioxane used) in toluene (3.09 g), and left to react at 105° C. for two hours. Following completion of the reaction, toluene and unreacted components were evaporated, and then toluene (10 g) was added again to dissolve the reaction product. Separately, vinyldiphenylmethylsilane (3.37 g, an amount such that the number of alkenyl groups is 0.29 per hydrosilyl group of the 1,3,5,7-tetrahydrogen-1,3,5,7-tetramethylcyclotetrasiloxane used) was dissolved in toluene (3.37 g), and combined with a xylene solution (0.56 μL) of a platinum-vinylsiloxane complex (platinum-vinylsiloxane complex containing 3 wt % of platinum, available from Umicore Precious Metals Japan Co., Ltd., Pt-VTSC-3X). The resulting solution was slowly added dropwise to the former solution, and left to react at 105° C. for one hour. Following completion of the reaction, ethynylcyclohexanol (1.99 μl) and dimethyl maleate (0.46 μl) were added and toluene was evaporated to give 10.4 g of a liquid modified polyhedral polysiloxane (SiH value: 1.43 mol/kg). To a 5.00 g portion of the obtained modified product was added 1,5-divinyl-3,3-diphenyl-1,1,5,5-tetramethyltrisiloxane (0.95 g), and the mixture was stirred to prepare a polyhedral polysiloxane composition. The composition thus obtained was evaluated by the above-mentioned methods. Table 1 shows the results.

Example 2

A 5.00 g portion of the tris(vinyldimethylsiloxy)-pentakis(trimethylsiloxy)octasilsesquioxane (an alkenyl group-containing polyhedral polysiloxane compound) prepared in Production Example 1 was dissolved in toluene (10.0 g), and combined with a xylene solution (0.48 μL) of a platinum-vinylsiloxane complex (platinum-vinylsiloxane complex containing 3 wt % of platinum, available from Umicore Precious Metals Japan Co., Ltd., Pt-VTSC-3X). The resulting solution was slowly added dropwise to a solution of 1,3,5,7-tetrahydrogen-1,3,5,7-tetramethylcyclotetrasiloxane (3.09 g, an amount such that the number of hydrosilyl groups is 4.0 per alkenyl group of the tris(vinyldimethylsiloxy)-pentakis(trimethylsiloxy)octasilsesquioxane used) in toluene (3.09 g), and left to react at 105° C. for two hours. The reaction solution was sampled and analyzed by NMR to confirm that no peak associated with the alkenyl group was present. Separately, vinyldiphenylmethylsilane (3.37 g, an amount such that the number of alkenyl groups is 0.29 per hydrosilyl group of the 1,3,5,7-tetrahydrogen-1,3,5,7-tetramethylcyclotetrasiloxane used) was dissolved in toluene (3.37 g), and combined with a xylene solution (0.56 µL) of a platinum-vinylsiloxane complex (platinum-vinylsiloxane complex containing 3 wt % of platinum, available from Umicore Precious Metals Japan Co., Ltd., Pt-VTSC-3X). The resulting solution was slowly added dropwise to the former solution, and left to react at 105° C. for one hour. Following completion of the reaction, ethynylcyclohexanol (1.99 µl) and dimethyl maleate (0.46 µl) were added and toluene and unreacted components were evaporated to give 11.2 g of a liquid modified polyhedral polysiloxane (SiH value: 1.73 mol/kg). To a 5.00 g portion of the obtained modified product was added 1,5-divinyl-3,3-diphenyl-1,1,5,5-tetramethyltrisiloxane (1.14 g), and the mixture was stirred to prepare a polyhedral polysiloxane composition. The composition thus obtained was evaluated by the above-mentioned methods. Table 1 shows the results.

Example 3

Vinyldiphenylmethylsilane (3.37 g, an amount such that the number of alkenyl groups is 0.29 per hydrosilyl group of the 1,3,5,7-tetrahydrogen-1,3,5,7-tetramethylcyclotetrasiloxane used) was dissolved in toluene (3.37 g), and combined with a xylene solution (0.56 µL) of a platinum-vinylsiloxane complex (platinum-vinylsiloxane complex containing 3 wt % of platinum, available from Umicore Precious Metals Japan Co., Ltd., Pt-VTSC-3X). The resulting solution was slowly added dropwise to a solution of 1,3,5,7-tetrahydrogen-1,3,5,7-tetramethylcyclotetrasiloxane (3.09 g, an amount such that the number of hydrosilyl groups is 4.0 per alkenyl group of the tris(vinyldimethylsiloxy)-pentakis(trimethylsiloxy)octasilsesquioxane used) in toluene (3.09 g), and left to react at 105° C. for one hour. The reaction solution was sampled and analyzed by NMR to confirm that no peak associated with the alkenyl group was present. Separately, a 5.00 g portion of the tris(vinyldimethylsiloxy)pentakis-(trimethylsiloxy)octasilsesquioxane (an alkenyl group-containing polyhedral polysiloxane compound) prepared in Production Example 1 was dissolved in toluene (10.0 g), and combined with a xylene solution (0.48 µL) of a platinum-vinylsiloxane complex (platinum-vinylsiloxane complex containing 3 wt % of platinum, available from Umicore Precious Metals Japan Co., Ltd., Pt-VTSC-3X). The resulting solution was slowly added dropwise to the former solution, and left to react at 105° C. for two hours. Following completion of the reaction, ethynylcyclohexanol (1.99 µl) and dimethyl maleate (0.46 µl) were added and toluene and unreacted components were evaporated to give 11.3 g of a liquid modified polyhedral polysiloxane (SiH value: 1.75 mol/kg). To a 5.00 g portion of the obtained modified product was added 1,5-divinyl-3,3-diphenyl-1,1,5,5-tetramethyltrisiloxane (1.15 g), and the mixture was stirred to prepare a polyhedral polysiloxane composition. The composition thus obtained was evaluated by the above-mentioned methods. Table 1 shows the results.

Example 4

A 5.00 g portion of the tris(vinyldimethylsiloxy)-pentakis(trimethylsiloxy)octasilsesquioxane (an alkenyl group-containing polyhedral polysiloxane compound) prepared in Production Example 1 was dissolved in toluene (16.73 g), and combined with vinyldiphenylmethylsilane (3.37 g, an amount such that the number of alkenyl groups is 0.29 per hydrosilyl group of the 1,3,5,7-tetrahydrogen-1,3,5,7-tetramethylcyclotetrasiloxane used) and a xylene solution (1.04 µL) of a platinum-vinylsiloxane complex (platinum-vinylsiloxane complex containing 3 wt % of platinum, available from Umicore Precious Metals Japan Co., Ltd., Pt-VTSC-3X). The resulting solution was slowly added dropwise to a solution of 1,3,5,7-tetrahydrogen-1,3,5,7-tetramethylcyclotetrasiloxane (3.09 g, an amount such that the number of hydrosilyl groups is 4.0 per alkenyl group of the tris(vinyldimethylsiloxy)pentakis(trimethylsiloxy)-octasilsesquioxane used) in toluene (3.09 g), and left to react at 105° C. for two hours. Following completion of the reaction, ethynylcyclohexanol (1.99 µl) and dimethyl maleate (0.46 µl) were added and toluene and unreacted components were evaporated to give 11.4 g of a liquid modified polyhedral polysiloxane (SiH value: 1.69 mol/kg). To a 5.00 g portion of the obtained modified product was added 1,5-divinyl-3,3-diphenyl-1,1,5,5-tetramethyltrisiloxane (1.12 g), and the mixture was stirred to prepare a polyhedral polysiloxane composition. The composition thus obtained was evaluated by the above-mentioned methods. Table 1 shows the results.

Comparative Example 1

A 5.00 g portion of the tris(vinyldimethylsiloxy)-pentakis(trimethylsiloxy)octasilsesquioxane (an alkenyl group-containing polyhedral polysiloxane compound) prepared in Production Example 1 was dissolved in toluene (10.0 g), and combined with a xylene solution (0.47 µL) of a platinum-vinylsiloxane complex (platinum-vinylsiloxane complex containing 3 wt % of platinum, available from Umicore Precious Metals Japan Co., Ltd., Pt-VTSC-3X). The resulting solution was slowly added dropwise to a solution of 1,3,5,7-tetrahydrogen-1,3,5,7-tetramethylcyclotetrasiloxane (3.09 g, an amount such that the number of hydrosilyl groups is 4.0 per alkenyl group of the tris(vinyldimethylsiloxy)-pentakis(trimethylsiloxy)octasilsesquioxane used) in toluene (3.09 g), and left to react at 105° C. for two hours. Following completion of the reaction, ethynylcyclohexanol (1.99 µl) and dimethyl maleate (0.46 µl) were added and toluene and unreacted components were evaporated to give 7.8 g of a liquid modified product (SiH value: 3.78 mol/kg). To the obtained modified product were added 1,5-divinyl-3,3-diphenyl-1,1,5,5-tetramethyltrisiloxane (2.20 g) and vinyldiphenylmethylsilane (2.90 g, an amount such that the number of alkenyl groups is 0.25 per hydrosilyl group of the 1,3,5,7-tetrahydrogen-1,3,5,7-tetramethylcyclotetrasiloxane used), and the mixture was stirred to prepare a composition. The composition thus obtained was evaluated by the above-mentioned methods. Table 1 shows the results.

Comparative Example 2

A 5.00 g portion of the tris(vinyldimethylsiloxy)-pentakis(trimethylsiloxy)octasilsesquioxane (an alkenyl group-containing polyhedral polysiloxane compound) prepared in Production Example 1 was dissolved in toluene (10.0 g), and combined with a xylene solution (0.47 µL) of a platinum-vinylsiloxane complex (platinum-vinylsiloxane complex containing 3 wt % of platinum, available from Umicore Precious Metals Japan Co., Ltd., Pt-VTSC-3X). The resulting solution was slowly added dropwise to a solution of 1,3,5,7-tetrahydrogen-1,3,5,7-tetramethylcyclotetrasiloxane (3.09 g, an amount such that the number of hydrosilyl groups is 4.0 per alkenyl group of the tris(vinyldimethylsiloxy)-pentakis(trimethylsiloxy)octasilsesquioxane used) in toluene (3.09 g), and left to react at 105° C. for two hours. Following completion of the reaction, ethynylcyclohexanol (1.99 µl) and dimethyl maleate (0.46 µl) were added and toluene and unreacted components were evaporated to give 7.8 g of a liquid modified product (SiH value: 3.78 mol/kg). To the obtained modified product was added 1,5-divinyl-3,3-diphenyl-1,1,5,5-tetramethyltrisiloxane (3.92 g), and the mixture was stirred to prepare a composition. The composition thus obtained was evaluated by the above-mentioned methods. Table 1 shows the results.

TABLE 1

|  | Example 1 | Example 2 | Example 3 | Example 4 | Comparative Example 1 | Comparative Example 2 |
|---|---|---|---|---|---|---|
| Viscosity (Pa · s) | 2.4 | 2.2 | 2.1 | 2.1 | 0.04 | 0.05 |
| Heat resistance test | Good | Good | Good | Good | Good | Good |
| Light resistance test | Good | Good | Good | Good | Good | Good |
| Thermal shock test | Good | Good | Good | Good | Good | Bad |
| Moisture permeability test | 10.6 | 11.8 | 11.1 | 11.4 | 11.2 | 16.2 |
| Sulfuration resistance test | Good | Good | Good | Good | Good | Intermediate |
| Phosphor settling test | Good | Good | Good | Good | Bad | Bad |

As seen in Table 1, the polyhedral polysiloxane compositions of the present invention which contained the components (A) and (B1) had high heat resistance and high light resistance, were excellent in thermal shock resistance and gas-barrier properties, and had a viscosity that ensures good handleability for encapsulating optical semiconductor devices.

Production Example 2

A 10.00 g portion of the tris(vinyldimethylsiloxy)-pentakis(trimethylsiloxy)octasilsesquioxane (an alkenyl group-containing polyhedral polysiloxane compound) prepared in Production Example 1 was dissolved in toluene (20.0 g), and combined with a xylene solution (0.94 µL) of a platinum-vinylsiloxane complex (platinum-vinylsiloxane complex containing 3 wt % of platinum, available from Umicore Precious Metals Japan Co., Ltd., Pt-VTSC-3X). The resulting solution was slowly added dropwise to a solution of 1,3,5,7-tetrahydrogen-1,3,5,7-tetramethylcyclotetrasiloxane (6.19 g, an amount such that the number of hydrosilyl groups is 4.0 per alkenyl group of the tris(vinyldimethylsiloxy)-pentakis(trimethylsiloxy)octasilsesquioxane used) in toluene (6.19 g), and left to react at 105° C. for two hours. Following completion of the reaction, toluene and unreacted components were evaporated, and then toluene (10.00 g) was added again to dissolve the reaction product. Separately, vinyldiphenylmethylsilane (5.78 g, an amount such that the number of alkenyl groups is 0.25 per hydrosilyl group of the 1,3,5,7-tetrahydrogen-1,3,5,7-tetramethylcyclotetrasiloxane used) was dissolved in toluene (5.78 g), and this solution was slowly added dropwise to the former solution. Following completion of the reaction, ethynylcyclohexanol (1.79 µl) and dimethylmaleate (0.41 µl) were added and toluene was evaporated to give 20.08 g of a liquid modified polyhedral polysiloxane (SiH value: 1.51 mol/kg).

Production Example 3

A 10.00 g portion of the tris(vinyldimethylsiloxy)-pentakis(trimethylsiloxy)octasilsesquioxane (an alkenyl group-containing polyhedral polysiloxane compound) prepared in Production Example 1 was dissolved in toluene (33.48 g), and combined with vinyldiphenylmethylsilane (6.74 g, an amount such that the number of alkenyl groups is 0.28 per hydrosilyl group of the 1,3,5,7-tetrahydrogen-1,3,5,7-tetramethylcyclotetrasiloxane used) and a xylene solution (0.94 µL) of a platinum-vinylsiloxane complex (platinum-vinylsiloxane complex containing 3 wt % of platinum, available from Umicore Precious Metals Japan Co., Ltd., Pt-VTSC-3X). The resulting solution was slowly added dropwise to a solution of 1,3,5,7-tetrahydrogen-1,3,5,7-tetramethylcyclotetrasiloxane (5.57 g, an amount such that the number of hydrosilyl groups is 3.6 per alkenyl group of the tris(vinyldimethylsiloxy)pentakis(trimethylsiloxy)-octasilsesquioxane used) in toluene (5.57 g), and left to react at 105° C. for two hours. Following completion of the reaction, ethynylcyclohexanol (1.79 µl) and dimethyl maleate (0.41 µl) were added and toluene and unreacted components were evaporated to give 21.46 g of a liquid modified polyhedral polysiloxane (SiH value: 1.55 mol/kg).

Example 5

A 10.00 g portion of the modified polyhedral polysiloxane prepared in Production Example 2 was combined with diallyl methyl isocyanurate (1.68 g), and the mixture was stirred to prepare a polyhedral polysiloxane composition. The composition thus obtained was evaluated by the above methods. Table 2 shows the results.

Example 6

A 10.00 g portion of the modified polyhedral polysiloxane prepared in Production Example 3 was combined with diallyl methyl isocyanurate (1.73 g), and the mixture was stirred to prepare a polyhedral polysiloxane composition. The composition thus obtained was evaluated by the above methods. Table 2 shows the results.

Example 7

A 10.00 g portion of the modified polyhedral polysiloxane prepared in Production Example 2 was combined with diallyl methyl isocyanurate (1.13 g) and 1,5-divinyl-3,3-diphenyl-1,1,5,5-tetramethyltrisiloxane (1.12 g), and the mixture was stirred to prepare a polyhedral polysiloxane composition. The composition thus obtained was evaluated by the above methods. Table 2 shows the results.

Example 8

A 10.00 g portion of the modified polyhedral polysiloxane prepared in Production Example 2 was combined with diallyl monoglycidyl isocyanurate (2.00 g), and the mixture was stirred to prepare a polyhedral polysiloxane composition. The composition thus obtained was evaluated by the above methods. Table 2 shows the results.

TABLE 2

|  | Example 5 | Example 6 | Example 7 | Example 8 |
|---|---|---|---|---|
| Viscosity (Pa · s) | 4.8 | 5.9 | 4.4 | 4.7 |
| Heat resistance test | Good | Good | Good | Good |
| Light resistance test | Good | Good | Good | Good |
| Thermal shock test | Good | Good | Good | Good |
| Moisture permeability test | 5.1 | 5.3 | 7.2 | 6.1 |
| Sulfuration resistance test | Good | Good | Good | Good |
| Phosphor settling test | Good | Good | Good | Good |

As seen in Table 2, the polyhedral polysiloxane compositions of the present invention which contained the components (A) together with the component (B2) or the components (B2) and (B1) had high heat resistance and high light resistance, and were excellent in thermal shock resistance and gas-barrier properties. Taking advantage of these properties, the polyhedral polysiloxane compositions of the present invention can be suitably used as encapsulants of various types. Such encapsulants can be used to fabricate optical devices, optical semiconductor devices, and the like.

The invention claimed is:

1. A polyhedral polysiloxane composition, comprising a modified polyhedral polysiloxane which is obtained by hydrosilylation of an alkenyl group-containing polyhedral polysiloxane compound (a) and an organic silicon compound (a') having one alkenyl group per molecule and at least one aryl group per molecule with a hydrosilyl group-containing compound (b), wherein the hydrosilyl group-containing compound (b) is a hydrosilyl group-containing cyclic siloxane and wherein the organic silicon compound (a') is a silane, wherein the polyhedral polysiloxane composition has a viscosity at 23° C. of not less than 1 Pa·s and up to 5.9 Pa·s; and the modified polyhedral polysiloxane, comprises a siloxane unit represented by the formula:

$$[XR^3{}_2SiO\text{—}SiO_{3/2}]_a[R^4{}_3SiO\text{—}SiO_{3/2}]_b$$

wherein a+b is an integer of 6 to 24, provided that a is an integer of 1 or larger and b is an integer of 0 or 1 or larger; $R^3$ is alkyl; $R^4$ is alkenyl, hydrogen, alkyl, or a group bonded to another polyhedral polysiloxane; and X has a structure represented by the following formula (2), and in the case where multiple Xs are present, the structures of the formula (2) may be different from one another;

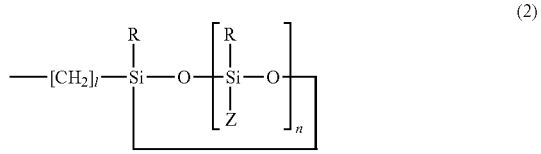

(2)

wherein l is an integer of 2 or larger; n is an integer of 2 or larger; Z is hydrogen, alkenyl, alkyl, aryl, or a moiety bonded to a polyhedral polysiloxane via an alkylene chain, and Zs may be the same as or different from one another, provided that at least one of Zs is hydrogen, and at least one of Zs has a structure represented by the formula (3):

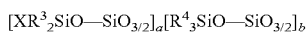

(3)

wherein l is an integer of 2 or larger, and $R^5$ is a group containing a silane having at least two aryl groups; and R is alkyl or aryl;
a phosphor; and
further comprising a compound (B) having at least two alkenyl groups per molecule.

2. The polyhedral polysiloxane composition according to claim 1, wherein the modified polyhedral polysiloxane is in liquid form at 20° C.

3. The polyhedral polysiloxane composition according to claim 1, wherein the aryl group is directly bonded to a silicon atom.

4. The polyhedral polysiloxane composition according to claim 1, wherein the hydrosilyl group-containing compound (b) is 1,3,5,7-tetrahydrogen-1,3,5,7-tetramethylcyclotetrasiloxane.

5. The polyhedral polysiloxane composition according to claim 1, wherein the alkenyl group-containing polyhedral polysiloxane compound (a) is an alkenyl group-containing polyhedral polysiloxane compound comprising a siloxane unit represented by the formula:

$$[AR^1{}_2SiO\text{—}SiO_{3/2}]_a[R^2{}_3SiO\text{—}SiO_{3/2}]_b$$

wherein a+b is an integer of 6 to 24, provided that a is an integer of 1 or larger and b is an integer of 0 or 1 or larger; A is alkenyl; $R^1$ is alkyl; and $R^2$ is hydrogen, alkyl, or a group bonded to another polyhedral polysiloxane.

6. The polyhedral polysiloxane composition according to claim 1, wherein the modified polyhedral polysiloxane has at least three hydrosilyl groups on average per molecule.

7. The polyhedral polysiloxane composition according to claim 1, wherein the compound (B) is a polysiloxane (B1) having at least two alkenyl groups per molecule.

8. The polyhedral polysiloxane composition according to claim 7, wherein the polysiloxane (B1) having at least two alkenyl groups per molecule has at least one aryl group.

9. The polyhedral polysiloxane composition according to claim 1, wherein the compound (B) is an organic compound (B2) represented by the following formula (4) and having at least two alkenyl groups per molecule:

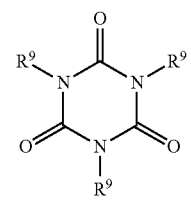

(4)

wherein $R^9$s each represent a monovalent $C_{1-50}$ organic group or hydrogen, and may be the same as or different from one another.

10. The polyhedral polysiloxane composition according to claim 9, wherein the organic compound (B2) has a number average molecular weight of less than 900.

11. The polyhedral polysiloxane composition according to claim 9, wherein the organic compound (B2) is at least one selected from the group consisting of triallyl isocyanurate, diallyl isocyanurate, diallyl monomethyl isocyanurate, and diallyl monoglycidyl isocyanurate.

12. The polyhedral polysiloxane composition according to claim 9, wherein the organic compound (B2) is diallyl monomethyl isocyanurate.

13. The polyhedral polysiloxane composition according to claim 1, comprising a hydrosilylation catalyst.

14. The polyhedral polysiloxane composition according to claim 1, comprising a cure retardant.

15. A cured product, obtained by curing the polyhedral polysiloxane composition according to claim 1.

16. An optical semiconductor device, comprising the polyhedral polysiloxane composition according to claim 1 as an encapsulant.

* * * * *